(12) United States Patent
Simhambhatla et al.

(10) Patent No.: US 7,011,842 B1
(45) Date of Patent: *Mar. 14, 2006

(54) POLYCATIONIC PEPTIDE COATINGS AND METHODS OF MAKING THE SAME

(75) Inventors: Murthy V Simhambhatla, San Jose, CA (US); Ni Ding, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 292 days.

This patent is subject to a terminal disclaimer.

(21) Appl. No.: 10/177,114

(22) Filed: Jun. 21, 2002

(51) Int. Cl.
*A61F 2/02* (2006.01)

(52) U.S. Cl. ..................... 424/426; 424/486
(58) Field of Classification Search ............... 424/426, 424/486
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,835,175 A | 9/1974 | Carpino et al. | 260/463 |
| 3,849,514 A | 11/1974 | Gray, Jr. et al. | 260/857 |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,908,404 A | 3/1990 | Benedict et al. | 525/54.11 |
| 4,917,309 A | 4/1990 | Zander et al. | 241/5 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,025,001 A | 6/1991 | Loscalzo et al. | 514/91 |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,155,137 A | 10/1992 | Keefer et al. | 514/611 |
| 5,163,952 A | 11/1992 | Froix | 623/1 |
| 5,165,919 A | 11/1992 | Sasaki et al. | 424/488 |
| 5,187,183 A | 2/1993 | Loscalzo et al. | 514/400 |
| 5,202,129 A | 4/1993 | Samejima et al. | 424/489 |
| 5,219,980 A | 6/1993 | Swidler | 528/272 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,356,890 A | 10/1994 | Loscalzo et al. | 514/210 |
| 5,366,997 A | 11/1994 | Keefer et al. | 614/611 |
| 5,380,299 A | 1/1995 | Fearnot et al. | 604/265 |
| 5,405,919 A | 4/1995 | Keefer et al. | 525/377 |
| 5,417,981 A | 5/1995 | Endo et al. | 424/486 |
| 5,424,077 A | 6/1995 | Lajoie | 424/641 |
| 5,428,070 A | 6/1995 | Cooke et al. | 514/557 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,482,720 A | 1/1996 | Murphy et al. | 424/489 |
| 5,485,496 A | 1/1996 | Lee et al. | 378/64 |
| 5,516,881 A | 5/1996 | Lee et al. | 528/320 |
| 5,536,723 A | 7/1996 | Loscalzo et al. | 514/247 |
| 5,543,099 A | 8/1996 | Zhang et al. | 264/115 |
| 5,569,463 A | 10/1996 | Helmus et al. | 424/426 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,639,441 A | 6/1997 | Sievers et al. | 424/9.3 |
| 5,644,020 A | 7/1997 | Timmermann et al. | 528/288 |

(Continued)

FOREIGN PATENT DOCUMENTS

DE   42 24 401   1/1994

(Continued)

OTHER PUBLICATIONS

Anonymous, Reducing the pH of a peptide oligomer to prepare for systemic delivery, Defensive Publication, Research Disclosure, p. 905 (Aug. 2003).

(Continued)

*Primary Examiner*—Carlos A. Azpuru

(74) *Attorney, Agent, or Firm*—Squire, Sanders & Dempsey, L.L.P.

(57) ABSTRACT

Polycationic peptide coatings for implantable medical devices and methods of making the same are described. The methods include applying an emulsion on the device, the emulsion including a polymer and a polycationic peptide. Other methods include incorporation of the polycationic peptide in microspheres and liposomes.

27 Claims, No Drawings

U.S. PATENT DOCUMENTS

| | | | |
|---|---|---|---|
| 5,649,977 A | 7/1997 | Campbell | 623/1 |
| 5,650,442 A | 7/1997 | Mitchell et al. | 514/611 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,804,318 A | 9/1998 | Pinchuk et al. | 428/421 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,852,058 A | 12/1998 | Cooke et al. | 514/564 |
| 5,854,376 A | 12/1998 | Higashi | 528/288 |
| 5,858,746 A | 1/1999 | Hubbell et al. | 435/177 |
| 5,861,168 A * | 1/1999 | Cooke et al. | 424/424 |
| 5,865,814 A | 2/1999 | Tuch | 604/265 |
| 5,869,127 A | 2/1999 | Zhong | 427/2.14 |
| 5,873,904 A | 2/1999 | Ragheb et al. | 623/1 |
| 5,874,165 A | 2/1999 | Drumheller | 428/308.4 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,891,459 A | 4/1999 | Cooke et al. | 424/439 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,945,452 A | 8/1999 | Cooke et al. | 514/564 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/291 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,060,534 A | 5/2000 | Ronan et al. | 523/113 |
| 6,063,432 A | 5/2000 | Maxwell et al. | 426/656 |
| 6,077,543 A | 6/2000 | Gordon et al. | 424/489 |
| 6,080,488 A | 6/2000 | Hostettler et al. | 428/423.3 |
| 6,095,134 A | 8/2000 | Sievers et al. | 128/200.14 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,117,872 A | 9/2000 | Maxwell et al. | 514/249 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,183,783 B1 | 2/2001 | Benoit et al. | 424/497 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,228,346 B1 | 5/2001 | Zhang et al. | 424/45 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,166 B1 | 10/2001 | Barry et al. | 623/1.46 |
| 6,306,176 B1 | 10/2001 | Whitbourne | 623/23.59 |
| 6,306,993 B1 | 10/2001 | Rothbard et al. | 526/304 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B1 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B1 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B1 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | 514/252.1 |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B1 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |

| Patent Number | Date | Inventor | Class |
|---|---|---|---|
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B1 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Hossainy et al. | 623/1.45 |
| 6,623,448 B1 | 9/2003 | Slater | 604/95.01 |
| 6,625,486 B1 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |
| 6,663,662 B1 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B1 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B1 | 3/2004 | Hossainy | 623/1.42 |
| 6,713,119 B1 | 3/2004 | Hossainy et al. | 427/2.25 |
| 6,716,444 B1 | 4/2004 | Castro et al. | 424/422 |
| 6,723,120 B1 | 4/2004 | Yan | 623/1.15 |
| 6,733,768 B1 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,746,481 B1 | 6/2004 | Larik et al. | |
| 6,749,626 B1 | 6/2004 | Bhat et al. | 623/1.1 |
| 6,753,071 B1 | 6/2004 | Pacetti et al. | 428/212 |
| 6,758,859 B1 | 7/2004 | Dang et al. | 623/1.15 |
| 6,759,054 B1 | 7/2004 | Chen et al. | 424/423 |
| 6,764,505 B1 | 7/2004 | Hossainy et al. | 623/1.15 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |

| | | |
|---|---|---|
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 04/009145 | 1/2004 |

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18 (12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Anderson et al., *Nitric-Oxide and Nitrovasodilators: Similarities, Differences and Potential Interactions*, JACC 24(2):555-566 (1994).

Anderson et al., *Close Relation of Endothelial Function in the Human Coronary and Peripheral Circulations*, JACC 26(5):1235-1241 (1995).

Bode-Boger et al., *Elevated L-Arginine/Dimethylarginine Ratio Contributes to Enhanced Systemic NO Production by Dietary L-Arginine in Hypercholesterolemic Rabbits*, Biochem. And Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al., *Asymmetric Dimethylarginine: A Novel Risk Factor for Endothelial Dysfunction*, Circ. 96(8):I-32 (1997).

Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).

Candipan et al., *Regression or Progression: Dependency on Vascular Nitric Oxide*, Arterioscler. Thromb. Vasc. Biol. 16(1):44-50 (1996).

Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).

Cooke et al., *Arginine: A New Therapy for Atherosclerosis?* Circ. 95(2):311-312 (1997).

Cooke et al., *Cytoprotective Effects of Nitric Oxide*, Circ. 88(5)1:2451-2454 (1993).

Cooke et al., *Derangements of the Nitric Oxide Synthase Pathway, L-Arginine, and Cardiovascular Diseases*, Circ. 96(2):379-382 (1997).

Cooke et al., *Diffuse Coronary Artery Disease and Endothelial Dysfunction: Form Follows Function*, ACC Curr. J. Rev. pp. 19-25 (Nov./Dec. 2000).

Cooke et al., *Regression and Progression: Dependency Upon NO* (Abstract), J. Investi. Med. 43(2) Suppl. 2:211A (1995).

Cooke et al., *The Role of Endothelium-Derived Nitric Oxide in Atherosclerosis*, Adv. Vasc. Path. 1150:3-14 (1997).

Cooke, *Does ADMA Cause Endothelial Dysfunction?*, Arterioscler. Thromb. Vasc. Biol. 20:2032-2037 (2002).

Cooke, *Enhancement of Endogenous Vascular Nitric Oxide: A New Therapeutic Strategy for Restenosis* (Abstract 301), Eur. J. Clin. Investi. 28:A53 (1998).

Cooke, *Is Atherosclerosis an Arginine Deficiency Disease?*, J. Investi. Med. 46(8):377-380 (1998).

Cooke, *Nutriceuticals for Cardiovascular Health*, Am. J. Cardio., 82(10A):43S-46S (1998).

Cooke, *Role of Nitric Oxide in Progression and Regression of Atherosclerosis*, West. J. Med. 164(5):419-424 (1996).

Cooke, *The 1998 Nobel Prize in Medicine: Clinical Implications for 1999 and Beyond*, Vasc. Med. 4:57-60 (1999).

Cooke, *The Endothelium: A New Target for Therapy*, Vasc. Med. 5:49-43 (2000).

Cooke, *The Pathophysiology Of Peripheral Arterial Disease: Rational Targets for Drug Intervention*, Vasc. Med. 2:227-230 (1997).

Creager et al., *L-Arginine Improves Endothelium-Dependent Vasodilation in Hypercholesterolemic Humans*, J. Clin. Investi. 90:1248-1253 (1992).

Drexler et al., *Effect of L-Arginine on Coronary Endothelial Function in Cardiac Transplant Recipients Relation to Vessel Wall Morphology*, Circ. 89(4):1615-1623 (1994).

Drexler et al., *Endothelial Dysfunction in the Coronary Circulation After Cardiac Transplantation: Effect of L-Arginine* (Abstract I356), Circ. 86(4) Supp:1418 (1992).

Dulak et al., *Nitric Oxide Induces the Synthesis of Vascular Endothelial Growth Factor by Rat Vascular Smooth Muscles Cells*, Arterioscler. Thromb. Vasc. Biol. 20:659-666 (2002).

http://www.lf2.cuni.dz/physiolres/1997/issue5/iss5cl6.html, Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).

Gaiser et al., *Lethal Short-Limbed Dwarfism in Transgenic Mice with an Arginine to Cysteine Substitution in Alpha-I (II) Procollagen* (Abstract 3369), Mol. Biol. Cell 7:579A (1996).

Ganz et al., *Coronary Vasospasm in Humans—The Role of Atherosclerosis and of Impaired Endothelial Vasodilator Function*, Basic Res. Cardiol. 86(Suppl 2):215-222 (1991).

Gregory et al., *Enhanced Nitric Oxide Production Induced by the Administration of L-Arginine Does Not Inhibit Arterial Neointimal Formation After Overwhelming Alloimmune Injury*, J. Heart Lung Transplant. 15(1)Part 1:58-66 (1966).

Gregory et al., *Nitric Oxide Induced by the Administration of L-Arginine Does Not Inhibit Arterial Neointimal Forma-* tion Following Alloimmune Injury (Abstract 41), J. Heart Lung Transplant. 14(1)Part 2:S45 (1995).

Heeschen et al., Hypercholesterolemia Impairs Angiogenic Response to Hind Limb Ischemia: Role of ADAM (Abstract 2490), Circ. I-473 (1999).

Ho et al., Dietary L-Arginine Reverses the Inhibitory Effect of Asymmetric Dimethylarginine on Angiogenesis in Hypercholesterolemia (Abstract 407-2), JACC 33:1A (1999).

Huet et al., Structural Homologies Between Two HLA B27-Restricted Peptides Suggest Residues Important for Interaction with HLA B27, Intl. Immunol. 2(4):311-316 (1990).

Hutchison et al., Effects of L-Arginine on Atherogenesis and Endothelial Dysfuntion Due to Secondhand Smoke, Hyperten. 34:44-50 (1999).

Jang et al., Angiogenesis is Impaired by Hypercholesterolemia: Role of Asymmetric Dimethylarginine, Circ. 102:1414-1419 (2000).

Jang et al., L-Arginine Reverses the Anti-Angiogenic Effects of Asymmetric Dimethylarginine (Abstract), J. Investi. Med. 4(2):86A (1999).

Jozkowicz et al., Genetic Augmentation of Nitric Oxide Synthase Increases the Vascular Generation of VEGF, Cardiovasc. Res. 51:773-783 (2001).

Kown et al., Arginine Polymers Inhibit Graft Coronary Artery Disease Following Cardiac Transplantation (Abstract 726), Transplant. 69(8):S300 (2000).

Kown et al., L-Arginine Polymers Inhibit the Development of Vein Graft Neointimal Hyperplasia, J. Thorac. Cardiovasc. Surg. 121(5):971-980 (2001).

Kown et al., L-Arginine Polymer Mediated Inhibition of Graft Coronary Artery Disease After Cardiac Transplantation, Transplant. 71(11):1542-1548 (2001).

Krejcy et al., Distribution and Metabolism of $N^G$-Nitro-L-Arginine and $N^G$-Nitro-L-Arginine Methylester in Canine Blood in vitro, Naunyn-Schmiedeberg's Arch. of Pharmacol. 347(3):342-345 (1993).

Krejcy et al., Metabolism of $L$-$N^G$-Nitro Arginine Methyl Ester in Human and Canine Plasma (Abstract 207), J. Mol. Cell. Cardiol. 24(Supp IV):S108 (1992).

Kyte et al., A Simple Method for Displaying the Hydropathic Character of a Protein, J. Mol. Biol. 157:105-132 (1982).

Latron et al., Positioning of a Peptide in the Cleft of HLA-A2 by Complementing Amino Acid Changes PNAS 88:11325-11329 (1991).

Lieberman et al., Estrogen Improves Endothelium-Dependent, Flow-Mediated Vasodilation in Postmenopausal Women, Annals Intern. Med. 121(12):936-941 (1994).

Lieberman et al., Flow-Induced Vasodilation of the Human Brachial Artery is Impaired in Patients <40 Years of Age with Coronary Artery Disease, Am. J. Cardiol. 78:1210-1214 (1996).

Lim et al., Acute Local Delivery of L-Arginine Reduces Long Term Intimal Thickening and Macrophage Infiltration (Abstract 2346), Circ. 94(8):I403 (1996).

Lin et al., Addition of a Poly Arginine Linker to Cyclosporin A Facilitates Transcutaneous Delivery and Topical Inhibition of Cutaneous Inflammation (Abstract 155), J. Inv. Derm. 114(4):777 (2000).

Lissin et al., Maintaining the Endothelium: Preventive Strategies for Vessel Integrity, Prev. Cardio. 3:172-177 (2000).

Maxwell et al., A Medical Food Designed to Enhance Nitric Oxide Activity Restores Endothelium-Dependent Function in Hypercholesterolemia (Abstract 140), Nitric Oxide: Biology and Chemistry 4(3):251(2000).

Maxwell et al., A Nutritional Product Designed to Enhance Nitric Oxide Activity Restores Endothelium-Dependent Function in Hypercholesterolemia, J. Investi. Med. 47(2): 45A (1999).

Maxwell et al., Cardiovascular Effects of L-Arginine, Curr. Opin. Nephrol. Hyperten. 7:63-70 (1998).

Maxwell et al., Endothelial Dysfunction in Hypercholesterolemia is Reversed by a Nutritional Product Designed to Enhance Nitric Oxide Activity, Cardiovasc. Drugs Therapy 14:309-316 (2000).

Maxwell et al., Improvement in Walking Distance and Quality of Life in Peripheral Arterial Disease by a Medical Food (Abstract 86), Nitric Oxide: Biology and Chemistry, 4(3): 232 (2000).

Maxwell et al., Improvement in Walking Distance and Quality of Life in Peripheral Arterial Disease by a Nutritional Product Designed to Enhance Nitric Oxide Activity (Abstract), J. Investi. Med. 47(2):63A (1999).

Maxwell et al., L-Arginine Attenuates the Impairment in Exercise Capacity Due to Hypercholesterolemia (Abstract), JACC 29:265A (1997).

Maxwell et al., L-Arginine Enhances Aerobic Exercise Capacity in Association with Augmented Nitric Oxide Production, J. Appl. Physiol. 90:933-938 (2001).

Maxwell et al., Limb Blood Flow During Exercise is Dependent on Nitric Oxide, Circ. 98:369-374 (1998).

Maxwell et al., Modulation of the Nitric Oxide Synthase Pathway in Atherosclerosis, Exp. Physiol. 83:573-584 (1998).

Maxwell et al., Nutritional Therapy for Peripheral Arterial Disease: A Double-Blind, Placebo-Controlled, Randomized Trial of HeartBar®, Vasc. Med. 5:11-19 (2000).

Maxwell et al., The Role of Nitric Oxide in Atherosclerosis, Cor. Art. Dis. 10:277-286 (1999).

Meredith et al., Role of Endothelium in Ischemic Coronary Syndromes, Am. J. Cardiol. 72(8):27C-32C (1993).

Meredith et al., Role of Impaired Endothelium-Dependent Vasodilation in Ischemic Manifestations of Coronary Artery Disease, Circ. 87(5) Suppl:V56-V66 (1993).

Mitchell et al.; Polyarginine Enters Cells More Efficiently than Other Polycationic Homopolymers, J. Peptide Res. 56:318-325 (2000).

Miyazaki et al., Endogenous Nitric Oxide Synthase Inhibitor: A Novel Marker of Atherosclerosis, Circ. 99:1141-1146 (1999).

http://pysiology.cup.cam.ac.uk/Proceedings/Abstracts/ 523P/Birmingham/Files/S32.html, Musialek et al., The Nitric Oxide Donor Sodium Nitroprusside Increases Heart Rate In The Absence Of Changes In Arterial Blood Pressure When Applied Topically To The Sino-Atrial Node In The Anaesthetized Pig, J. Physiol. (2000), printed Jun. 12, 2001.

Niebauer et al., Effects of Chronic Exercise in Patients with Chronic Heart Failure on Markers of Oxidative Stress (Abstracts 1019-10), JACC 33:172A (1999).

Niebauer et al., Endothelium-Derived Nitric Oxide Attenuates Monocyte-Endothelial Interaction in Chronic Hypercholesterolemia (Abstract 2014) Circ. 92(8)Suppl I:I-422 (1995).

Niebauer et al., Endotoxin and Immune Activation in Chronic Heart Failure: A Prospective Cohort Study, Lancet 353:1838-1842 (1999).

Niebauer et al., *Gene Transfer of Nitric Oxide Synthase: Effects on Endothelial Biology*, JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:I-551 (1997).

Niebauer et al., *Local L-Arginine Delivery After Balloon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Ohno et al., *Shear Stress Elevates Endothelial cGMP: Role of a Potassium Channel and G Protein Coupling*, Circ. 88:193-197 (1993).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide*, Intl. Immunol. 1(4):487-495 (1989).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain*, J. Exp. Med. 159:1351-1370 (1984).

Schwarzacher et al., *L-$N^G$-Nitro-Arginine Methyl Ester in the Anesthetized Rabbit: Venous Vasomotion and Plasma Levels*, J. Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone in vivo Using Intravascular Ultrasound*, J. Pharmacol, Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads to Enhanced Venous Reactivity in vivo*, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty*, Circ. 95(7):1863-1869 (1997).

Schwarzacher, *New Therapeutic Approaches for Correction of Endothelial Function After Balloon Dilatation* (Eng. Abstract), J Kardiologie 7(1):14-17 (2000).

Schwarzacher et al., *Altered Reactivity of the Inferior Vena Cava to Noradrenaline and Acetylcholine Following the Blockade of EDRF-Biosynthesis with $N^G$-Nitro-$_L$-Arginine Methyl Ester*, Clin. Exp. Pharmacol. Physiol. 23(6/7):490-492.

Selwyn et al., *Pathophysiology of Ischemia in Patients with Coronary Artery Disease*, Prog. Cardiovasc. Dis. XXXV(1):27-39 (1992).

http://www.pharmsci.org/scientificjournals/pharmsci/journal/99_7.html, Shameem et al., *A Short Term (Accelerated Release) Approach to Evaluate Peptide Release from PLGA Depot-Formulations*, Published Jul. 21, 1999, printed Feb. 19, 2002.

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract I20), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl:1942 (1992).

Singer et al., *Dietary Supplements of L-Arginine Reduce Atherogenesis and Alter Vascular Reactivity in Hypercholesterolemic Animals* (Abstract) Clin. Res. 41(1):78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).

Tangphao et al., *Diurnal Variation of Plasma L-Arginine Concentrations and The Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans in Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by The NO Precursor* (Abstract 765-4), JACC 25:276A (1995).

Todd et al., *Regulation of Loblolly Pine (Pinus taeda L.) Arginase in Developing Seedling Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enhanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).

von der Leyen et al., *Gene Therapy Inhibiting Neointimal Vascular Lesion:* in vivo *Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase As an* in vivo *Gene Transfer Approach to Prevent Neointima Formation After Vascular Injury*, Clin. Res. 42(2):180A (1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product/html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine In Cardiovascular Health*, U.S. Pharmacist Continuing Education, printed Sep. 12, 2002.

* cited by examiner

POLYCATIONIC PEPTIDE COATINGS AND METHODS OF MAKING THE SAME

BACKGROUND OF THE INVENTION

1. Field of the Invention

This invention relates to the field of implantable medical devices, such as stents. More particularly, this invention is directed to coatings for devices, the coatings including peptides such as polymers and/or oligomers of L-arginine.

2. Description of the Background

In the field of medical technology, there is frequently a necessity to administer a therapeutic substance locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results. For the treatment of vascular occlusions, such as restenosis, stents are being modified to administer therapeutic substances locally. One method of medicating a stent is with the use of a polymer coating impregnated with a therapeutic substance. The coating allows for the sustained release of the substance at the treatment site. L-arginine, or polypeptide oligomeric derivatives or analogs thereof, for example, those containing 5 to 20 amino acid units are one example of a therapeutic substance that can be used in conjunction with a stent.

L-arginine is a known precursor of endothelium derived nitric oxide (NO). NO is synthesized from L-arginine, or its polymeric and/or oligomeric derivatives, by the enzyme NO synthase oxygenase, a homodimeric flavo-hemoprotein that catalyzes the 5-electron oxidation of L-arginine to produce NO and L-citrulline. Among other therapeutic properties, NO regulates vascular tone, inhibits platelet aggregation, and inhibits vascular smooth muscle proliferation. These therapeutic properties are believed to contribute to the reduction or elimination of neo-intimal hyperplasia in vascular injury models.

U.S. Pat. No. 5,861,168 to Cooke et al. teaches that NO activity is reduced after vascular injury. Cooke et al. also teach that administering L-arginine as the NO precursor helps to restore vascular NO activity in patients with endothelial vasodilator dysfunction due to restenosis. It has been also taught that oligomeric peptides comprising 6 to 15 units of L- or D-arginine can be effective transfectors of cells (see, Mitchell, et al., *J. Peptide Res.*, vol. 56, p. 318 (2000)) and, using a rabbit vein-graft model, it has been demonstrated that oligomers of L- or D-arginine can inhibit vascular smooth cell proliferation by efficiently transfecting cells. See, Uemura, et al., *Circulation*, vol. 102, p. 2629 (2000). Using the rabbit model, it has also been shown that intramural administration of L-arginine inhibits lesion formation in a hypercholesterolemic balloon injury. See, Schwarzacher et al. *Circulation*, vol. 95, p. 1863 (1997).

Accordingly, it is desirable to incorporate L-arginine, or its polymers and/or oligomers into a stent coating. The present application describes the methods that can be used to achieve this goal.

SUMMARY

A method of coating an implantable medical device is provided. The method comprises applying an emulsion of a polymer and a polycationic peptide on the device to form a coating for the device. The device can be, for example, is a stent. The polycationic peptide can be poly(L-arginine), poly(D-arginine), poly(D,L-arginine), a racemic mixture of poly(L-arginine) and poly(D-arginine), poly(L-lysine), poly (D-lysine), poly($\delta$-guanidino-$\alpha$-aminobutyric acid), or mixtures thereof.

The polymer can be, for example, an acrylic polymer, a vinyl polymer, a polyurethane, or a combination thereof. Representative examples of the acrylic polymer include poly(butyl methacrylate) and poly(methyl methacrylate). Representative examples of the vinyl polymer include poly (ethylene-co-vinyl alcohol) and poly(vinyl acetate). In one embodiment, the emulsion can include first surfactant. This first surfactant can have hydrophilic-lipophilic balance between about 3 and about 6. The emulsion can additionally include a second surfactant having has a hydrophilic-lipophilic balance exceeding the value of 10.

A method for incorporating a polycationic peptide into a coating for an implantable medical device, e.g., a stent, is provided comprising fabricating microspheres containing the polycationic peptide; dispersing the microspheres in a polymer solution; and applying the solution onto the device. The fabrication of the microspheres can include emulsification of an aqueous solution of the polycationic peptide in an organic solvent medium. The organic solvent medium can be, for example, cyclooctane, cyclohexane, cycloheptane, para-xylene, dimethylformamide, dimethylsulfoxide, chloroform, methylene oxide, dimethylacetamide, and mixtures thereof.

A method for incorporating a polycationic peptide into a coating for an implantable medical device is provided, comprising: fabricating liposomes containing the polycationic peptide; dispersing the liposomes in a polymer solution; and applying the solution onto the device. The fabrication of the liposomes car include suspending a lipid in an aqueous medium solution in the presence of the polycationic peptide. The lipid can be phosphatidyl choline.

A medical device, such as a stent is also disclosed comprising a coating, the coating including a polymer phase and a polycationic peptide phase separate and distinguishable from the polymer phase.

DETAILED DESCRIPTION

L-arginine, also known as 2-amino-5-guanidinovaleric acid, is an amino acid having a formula $NH=C(NH_2-NH-CH_2-CH_2-CH_2-CH(NH_2)-COOH$. Polymers and/or oligomers of L-arginine that can be used are hereinafter referred to as "PArg" which comprise a plurality of repeating monomeric amino acid units connected with peptide bonds. PArg has a general formula $H[NH-CHX-CO]_p-OH$, where "p" can be within a range of 5 and 1,000, typically, within a range of between 6 and 20. For example, a heptamer (designated R7), having p=7, can be used. In the formula of PArg "X" is 1-guanidinopropyl radical having the structure $-CH_2-CH_2-CH_2-NH-C(NH_2)=NH$. The terms "polymers and/or oligomers of L-arginine," "poly-L-arginine," and "PArg" are intended to include L-arginine in both its polymeric and oligomeric form.

In addition to PArg, other polycationic peptides can be incorporated into the stent coatings. Examples of alternative polycationic peptides include racemic mixtures of poly(L-arginine), poly(D-arginine), racemic mixtures of poly(D-arginine), poly(L-lysine), poly(D-lysine), and poly($\delta$-guanidino-$\alpha$-aminobutyric acid). Those having ordinary skill in the art may choose to use other appropriate peptides if desired.

Coating Stents with Polypeptide-Containing Emulsions

In accordance with one embodiment, an emulsion containing a polymer and a polypeptide, for example, R7 is prepared. To make the emulsion, R7 can be dissolved in water to form the aqueous phase (solution I). The concentration of R7 in solution I can be between about 5 and 15 mass %. A polymer is then dissolved in a suitable organic solvent, such as dimethylformamide, dimethylsulfoxide, chloroform, methylene chloride, or dimethylacetamide, to form the organic phase (solution II). The concentration of the polymer in solution II can be between about 1 and 15 mass %.

One example of the polymer that can be used for making the organic phase is poly(ethylene-co-vinyl alcohol), the copolymer of ethylene and vinyl alcohol also known under the trade name EVAL and distributed commercially by Aldrich Chemical Company of Milwaukee, Wis. EVAL is also manufactured by EVAL Company of America of Lisle, Ill. EVAL has the general formula —$[CH_2—CH_2]_m$—$[CH_2—CH(OH)]_n$—. EVAL is a product of hydrolysis of ethylene-vinyl acetate copolymers. Those having ordinary skill in the art of polymer chemistry will understand that EVAL may also be a terpolymer and may include up to 5% (molar) of units derived from styrene, propylene and other suitable unsaturated monomers.

Other polymers can be used in lieu of or in addition to EVAL to for preparation of solution II. Examples of such polymers include other vinyl polymers such as poly(vinyl acetate) (PVA), acrylic polymers such as poly(butyl methacrylate) (PBMA) or poly(methyl methacrylate) (PMMA), polyurethanes, and combinations thereof.

The organic phase can also optionally include a surfactant or a mixture of surfactants. The surfactant or the mixture of surfactants can have a hydrophilic-lipophilic balance (HLB) within a range of between about 3 and about 6. Examples of suitable surfactants having HLB between 3 and 6 include SPAN 80 (sorbitan oleate), SPAN 60 (sorbitan monostearates), ARLACEL 83 (sorbitan sesquioleate), TX-4 (polyoxyethylene alkylphenol ether), MOA-3 (polyoxyethylene aliphatic alcohol ether), polyoxamers such as poly(ethylene oxide)-poly(propylene oxide)-poly(ethylene oxide) block-copolymer, egg lechitin, BRIJ 93 (polyoxyethylene oleyl ether), IGEPAL CO-210 (polyoxyethylene nonyl phenyl ether), propylene glycol monostearate, propylene glycol monolaurate, glycerol monolaurate and mixtures thereof.

Surfactants having high HLB (>10) can be also blended with low HLB surfactants described above. Example of suitable high HLB surfactants include TWEEN 20 and TWEEN 21 (polyoxyethylene sorbitan monolaurates), TWEEN 80 (polyoxyethylene sorbitan monooleate), TWEEN 85 (polyoxyethylene sorbitan trioleate), BRIJ 76 and BRIJ 78 (polyoxyethylene stearyl ethers). TWEEN, SPAN, BRIJ, ARLACEL and IGEPAL are trade names of the surfactants. TWEEN, SPAN, BRIJ and ARLACEL are available from ICI Americas, Inc. of Bridgewater, N.J. IGEPAL is available from Rhone-Poulenc, Inc. of Cranbury, N.J.

Solution I is added to solution II and the mixture is sonicated or homogenized to make the water-in-oil emulsion. "Sonication" is defined as agitation by high-frequency sound waves applied to the mixture. The conditions under which the sonication or homogenization is carried out can be determined by one having ordinary skill in the art. The ratio between solution I and solution II can be between about 1:9 and about 1:1 by volume. The R7-containing emulsion can then be applied to a stent by any conventional technique, for example, by spraying or dipping, to form the reservoir matrix of the stent coating. The amount of R7 in this layer can be between about 10 and 200 micrograms.

Optionally, a therapeutic agent or a drug can be incorporated into the coating, for example by dispersing or dissolving the drug in solution I or II prior to mixing the solutions. The agent could be for inhibiting the activity of vascular smooth muscle cells. It can be directed at inhibiting abnormal or inappropriate migration and/or proliferation of smooth muscle cells to inhibit restenosis. The active agent can include any substance capable of exerting a therapeutic or prophylactic effect in the practice of the present invention. The drug may include small molecule drugs, peptides, proteins, oligonucleotides, or double-stranded DNA. The active agent can also be conjugated to R7 either by covalent attachment or by ionic interaction.

Examples of the drugs include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrirnidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

Prior to the application of the reservoir layer, a polymer primer layer can be formed on the bare stent. The polymers for the optional primer layer can be the same polymers that are used to make the reservoir layer.

The coated stent can be optionally freeze-dried to remove the residual solvent and/or moisture. The process of freeze-drying can be carried out using techniques and equipment known to those having ordinary skill in the art. Also, the R7-coated stent can be over-coated with a diffusion limited hydrophobic polymer topcoat if desired. The use of the topcoat is optional. The polymers used for fabrication of the topcoat can include poly(vinylidene fluoride), PBMA, PMMA, or combinations thereof.

Coating Stents with Polymer Compositions Containing Microspheres or Liposomes In accordance with other embodiments, microspheres or liposomes containing a polypeptide, for example R7, can be dispersed in a polymer composition. The polymer composition, containing the microspheres incorporating R7, is then applied to the stent.

In accordance with one embodiment, an encapsulating polymer is dissolved in a suitable organic solvent such as methylene chloride, cyclooctane, cyclohexane, cycloheptane, para-xylene, dimethylformamide, dimethylsulfoxide, chloroform, dimethylacetamide, or mixtures thereof. The encapsulating polymers can include EVAL, other vinyl polymers such as poly(vinyl acetate) (PVA), acrylic polymers such as poly(butyl methacrylate) (PBMA) or poly(methyl methacrylate) (PMMA), polyurethanes, poly(L-lactide), poly(D,L-lactide), poly(glycolide), poly(caprolactone), polyanhydrides, polydiaxanone, polyorthoesters, polyamino acids, poly(trimethylene carbonate), and combinations thereof. The R7 is then added to the polymer solution either as an aqueous solution containing an emulsifying agent such as poly(vinyl alcohol), or as a solid dispersion, and stirred, homogenized or sonicated to create a primary emulsion of R7 in the polymer phase. Surfactants such as poly(vinyl alcohol), albumin (either bovine or human serum), gelatin, lipophilic emulsifiers such as PLURONIC or TETRONIC, or a combination thereof can be optionally added to stabilize the primary emulsion. PLURONIC is a trade name of poly(ethylene oxide-co-propylene oxide). TETRONIC is a trade name of a family of non-ionic tetrafunctional block-copolymer surfactants. PLURONIC and TETRONIC are available from BASF Corp. of Parsippany, N.J.

The primary emulsion is stirred with an aqueous solution containing an emulsifying agent such as poly(vinyl alcohol) to create a secondary emulsion of protein containing polymer in the aqueous phase. The secondary emulsion is stirred in excess water, optionally under vacuum to remove the organic solvent and harden the microspheres. The hardened microspheres are collected by filtration or centrifugation and lyophilized.

According to another technique, a primary emulsion of R7 in an aqueous phase is formed as in the first technique described above. This emulsion is then stirred with a non-solvent for the polymer, such as silicone oil to extract the organic solvent and form embryonic microspheres of polymer with trapped R7. The non-solvent is then removed by the addition of a volatile second non-solvent such as heptane, and the microspheres harden. The hardened microspheres are collected by filtration or centrifugation and lyophilized.

According to yet another technique, the R7, formulated as lyophilized powder is suspended in a polymer phase consisting of polymer dissolved in a volatile organic solvent such as methylene chloride. The suspension is then spray dried to produce polymer microparticles with entrapped R7.

According to yet another technique, the R7, formulated as a powder is suspended in a polymer phase consisting of polymer dissolved in a volatile organic solvent such as methylene chloride. The suspension is sprayed into a container containing frozen ethanol overlaid with liquid nitrogen. The system is then warmed to about −70° C. to liquefy the ethanol and extract the organic solvent from the microspheres. The hardened microspheres are collected by filtration or centrifugation and lyophilized.

Liposomes are aqueous compartments pouches which are typically made of phospholipids. Liposomes can be fabricated according to standard techniques known to those having ordinary skill in the art. One way of forming of the liposome can be by suspending a suitable lipid, such as phosphatidyl choline in an aqueous medium followed by sonication of the mixture. An alternative way of preparing the lipid vesicles can be by rapidly mixing a solution of the lipid in an ethanol-water blend, for example, by injecting the lipid through a needle into a agitated ethanol-water solution. Besides phospholipids, other amphophilic substances can be used, for example, shingomyelin or lipids containing polymerized portions of poly(ethylene glycol). Liposomes having a diameter of about 500 Angstroms can be fabricated.

To trap R7 inside the liposomes, the liposomes can be formed in the presence of R7. For example, in the process of forming the liposomes described above, the aqueous or ethanol-water medium can contain R7. R7 can be dissolved in the medium. For example, if 500 Angstrom vesicles are formed in an approximately decimolar solution of R7 (i.e., the concentration of R7 in the medium is about 0.1 moles per liter), about 2,000 molecules of R7 can be trapped in the inner compartment of each liposome. Following the formation of the R7-filled lipid vesicles, the vesicles can be separated from the surrounding solution and purified, for example, by dialysis or gel-filtration chromatography. Other suitable methods of separation can be employed as is understood by one having ordinary skill in the art.

The R7-containing microspheres or liposomes can then be dispersed in a solution of an appropriate polymer to form a polymer-microsphere or polymer-liposome suspension. The mass ratio between the liposome and the polymer in the suspension can be within a range of between about 1:5 and 1:2. Examples of polymers that can be used, include, but are not limited to, EVAL, other vinyl polymers such as PVA, acrylic polymers such PBMA or PMMA, polyurethanes, and combinations thereof.

The coatings and methods of the present invention have been described in conjunction with a stent. The stent can be used in any part of the vascular system, including neurological, carotid, coronary, renal, aortic, iliac, femoral or any other peripheral vascular sites. The stent can be balloon-expandable or self-expandable. There are no limitations on the size of the stent, its length, diameter, strut thickness or pattern. The use of the coating is, however, not limited to stents and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating an implantable medical device, comprising applying an emulsion of a polymer and a polycationic peptide on the device to form a coating for the device.

2. The method of claim 1, wherein the device is a stent.

3. The method of claim 1, wherein the polycationic peptide includes poly(L-arginine), poly(D-arginine), poly(D,L-arginine), a mixture of poly(L-arginine) and poly(D-arginine), poly(L-lysine), poly(D-lysine), poly(δ-guanidino-α-aminobutyric acid), or mixtures thereof.

4. The method of claim 1, wherein the polymer comprises an acrylic polymer, a vinyl polymer, a polyurethane, or a combination thereof.

5. The method of claim 4, wherein the acrylic polymer is selected from a group consisting of poly(butyl methacrylate) and poly(methyl methacrylate).

6. The method of claim 4, wherein the vinyl polymer is selected from a group consisting of poly(ethylene-co-vinyl alcohol) and poly(vinyl acetate).

7. The method of claim 1, wherein the emulsion further comprises a first surfactant.

8. The method of claim 7, wherein the first surfactant has a hydrophilic-lipophilic balance between about 3 and about 6.

9. The method of claim 8, wherein the emulsion additionally comprises a second surfactant having has a hydrophilic-lipophilic balance exceeding the value of 10.

10. The method of claim 1, wherein the emulsion is a water-in-oil emulsion.

11. A coating for an implantable medical device, the coating fabricated by the method of claim 1.

12. A method for incorporating a polycationic peptide into a coating for an implantable medical device, the method comprising:
(a) fabricating microspheres containing the polycationic peptide;
(b) dispersing the microspheres in a polymer solution; and
(c) applying the solution onto the device.

13. The method of claim 12, wherein the medical device is a stent.

14. The method of claim 12, wherein the polycationic peptide includes poly(L-arginine), poly(D-arginine), poly(D,L-arginine), a mixture of poly(L-arginine) and poly(D-arginine), poly(L-lysine), poly(D-lysine), poly(δ-guanidino-α-aminobutyric acid), or mixtures thereof.

15. The method of claim 12, wherein the fabrication of the microspheres includes emulsification of an aqueous solution of the polycationic peptide in an organic solvent medium.

16. The method of claim 15, wherein the organic solvent is selected from a group consisting of cyclooctane, cyclohexane, cycloheptane, para-xylene, dimethylformamide, dimethylsulfoxide, chloroform, methylene oxide, dimethylacetamide, and mixtures thereof.

17. The method of claim 12, wherein a polymer in the polymer solution is selected from the group consisting of poly(ethylene-co-vinyl alcohol), poly(vinyl acetate), poly(butyl methacrylate), poly(methyl methacrylate), poly(urethane), poly(L-lactide), poly(D,L-lactide), poly(glycolide), poly(caprolactone), polyanhydrides, polydiaxanone, polyorthoesters, polyamino acids, poly(trimethylene carbonate), and combinations thereof.

18. A coating for an implantable medical device, the coating fabricated by the method of claim 12.

19. A method for incorporating a polycationic peptide into a coating for an implantable medical device, the method comprising:
(a) fabricating liposomes containing the polycationic peptide;
(b) dispersing the liposomes in a polymer solution; and
(c) applying the solution onto the device.

20. The method of claim 19, wherein the medical device is a stent.

21. The method of claim 19, wherein the polycationic peptide includes poly(L-arginine), poly(D-arginine), poly(D,L-arginine) a mixture of poly(L-arginine) and poly(D-arginine), poly(L-lysine), poly(D-lysine), poly(δ-guanidino-α-aminobutyric acid), or a mixture thereof.

22. The method of claim 19, wherein the fabrication of the liposomes includes suspending a lipid in an aqueous medium solution in the presence of the polycationic peptide.

23. The method of claim 22, wherein the lipid is phosphatidylcholine.

24. The method of claim 22, further comprising isolation and purification of the liposomes.

25. The method of claim 24, wherein the isolation and purification is achieved by dialysis or gel-filtration chromatography.

26. The method of claim 19, wherein a polymer in the polymer solution is selected from the group consisting of poly(ethylene-co-vinyl alcohol), poly(vinyl acetate), poly(butyl methacrylate), poly(methyl methacrylate), and poly(urethane).

27. A coating for an implantable medical device, the coating fabricated by the method of claim 19.

* * * * *